United States Patent [19]

Daum et al.

[11] Patent Number: 4,914,123
[45] Date of Patent: Apr. 3, 1990

[54] ACYLOXYTHIOPHENE DERIVATIVES

[75] Inventors: Werner Daum, Krefeld; Erich Klauke, Odenthal; Engelbert Kühle, Bergisch-Gladbach; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 690,930

[22] Filed: Jan. 11, 1985

[30] Foreign Application Priority Data

Jan. 26, 1984 [DE] Fed. Rep. of Germany ....... 3402625

[51] Int. Cl.[4] .................... A01N 43/02; C07D 333/32
[52] U.S. Cl. .......................................... 514/445; 549/64
[58] Field of Search ............................ 549/64; 514/445

[56] References Cited

U.S. PATENT DOCUMENTS 4,421,761 12/1983 Nagai et al. .......................... 549/64

FOREIGN PATENT DOCUMENTS 0032748 1/1981 European Pat. Off. ............... 549/64
0093384 11/1983 European Pat. Off. ............... 549/64

*Primary Examiner*—Alan Siegel
*Attorney, Agent, or Firm*—Sprung Horn Kramer & Woods

[57] ABSTRACT

Acyloxythiophenes of the formula

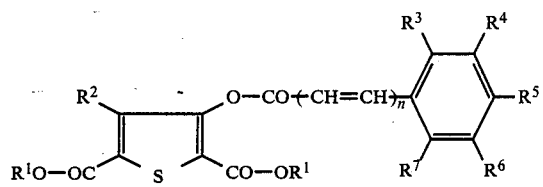

in which
$R^1$ represents alkyl, alkoxyalkyl, alkylthioalkyl, halogenoalkyl, cyanoalkyl, trialkylsilylmethyl, alkenyl or alkinyl,
$R^2$ represents alkyl,
n represents 0 or 1 and
$R^3$ to $R^5$ are identical or different and represent hydrogen, alkyl, alkoxy, halogenoalkyl, halogenoalkoxy, halogenoalkylthio, halogenoalkylsulphinyl, halogenoalkylsulphonyl, N-halogenoalkyl-N-halogenoalkylthioamino, chlorine or fluorine and
$R^6$ and $R^7$ represent hydrogen, fluorine, chlorine, nitro or trifluoromethyl, with the proviso that one of the radicals $R^3$ to $R^7$ is a fluorine-containing radical or at least 3 of the radicals $R^3$ to $R^7$ represent fluorine and/or chlorine, which possess fungicidal activity.

2 Claims, No Drawings

ACYLOXYTHIOPHENE DERIVATIVES

The present invention relates to new acyloxythiophene derivatives, a process for their preparation and their use as plant protection agents, in particular as fungicides.

It is already known that thiophene derivatives, such as, for example, 2,5-bis-(butoxycarbonyl)-3-methyl-4-styrylcarbonyloxy-thiophene and 2,5-bis-ethoxycarbonyl-3,4-bis-benzoyloxy-thiophene, have fungicidal properties (compare European Patent 93,384 and European Patent 32,748).

Under certain circumstances, for example when low amounts and concentrations are applied, the action of these compounds may not always be completely satisfactory.

New acyloxythiophene derivatives of the general formula (I)

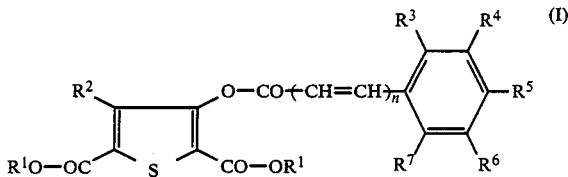

in which
R$^1$ represents alkyl, alkoxyalkyl, alkylthioalkyl, halogenoalkyl, cyanoalkyl, trialkylsilylmethyl, alkenyl or alkinyl,
R$^2$ represents alkyl,
n represents 0 or 1 and
R$^3$ to R$^5$ are identical or different and represent hydrogen, alkyl, alkoxy, halogenoalkyl, halogenoalkoxy, halogenoalkylthio, halogenoalkylsulphinyl, halogenoalkylsulphonyl, N-halogenoalkyl-N-halogenoalkylthioamino, chlorine or fluorine and
R$^6$ and R$^7$ represent hydrogen, fluorine, chlorine, nitro or trifluoromethyl, with the proviso that one of the radicals R$^3$ to R$^7$ is a fluorine-containing radical or at least 3 of the radicals R$^3$ to R$^7$ represent fluorine and/or chlorine,
have been found.

It has furthermore been found that the new acyloxythiophene derivatives of the general formula (I)

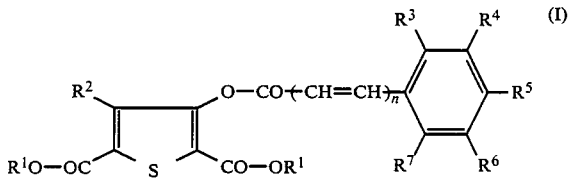

in which
R$^1$ represents alkyl, alkoxyalkyl, alkylthioalkyl, halogenoalkyl, cyanoalkyl, trialkylsilylmethyl, alkenyl or alkinyl,
R$^2$ represents alkyl,
n represents 0 or 1 and
R$^3$ to R$^5$ are identical or different and represent hydrogen, alkyl, alkoxy, halogenoalkyl, halogenoalkoxy, halogenoalkylthio, halogenoalkylsulphinyl, halogenoalkylsulphonyl, N-halogenoalkyl-N-halogenoalkylthioamino, chlorine or fluorine and
R$^6$ and R$^7$ represent hydrogen, fluorine, chlorine, nitro or trifluoromethyl, with the proviso that one of the radicals R$^3$ to R$^7$ is a fluorine-containing radical or at least 3 of the radicals R$^3$ to R$^7$ represent fluorine and/or chlorine,
are obtained by a process in which a carboxylic acid derivative of the general formula (II)

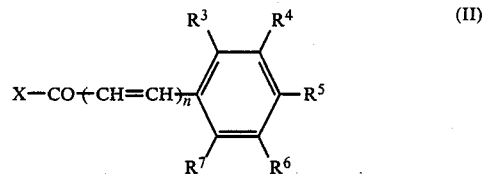

in which
X represents halogen, hydroxyl or the radical

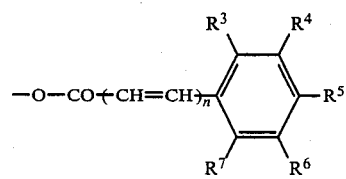

wherein, in the formulae,
n and R$^3$ to R$^7$ have the abovementioned meaning,
is reacted with 3-hydroxy-thiophene derivatives of the general formula (III)

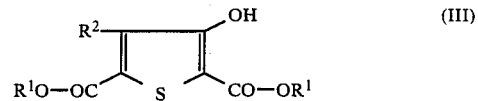

in which
R$^1$ and R$^2$ have the abovementioned meaning,
if appropriate in the presence of a solvent or diluent and if appropriate in the presence of an acid-binding agent or dehydrating agent.

It has furthermore been found that the new acyloxythiophene derivatives of the formula (I) have fungicidal properties.

Surprisingly, the acyloxythiophene derivatives of the formula (I) according to the invention exhibit a better fungicidal activity than the fungicides known from the prior art, such as, for example, 2,5-bis-(isopropoxycarbonyl)-3-methyl-4-(3-methylbenzoyloxy)-thiophene, 2-sec.-butyl-4,6-dinitrophenyl 3-methylcrotonate and/or the 6-methyl-2-oxo-1,3-dithiolo-[4,5-b]-quinoxaline.

Formula (I) provides a general definition of the acyloxythiophene derivatives according to the invention. Preferred compounds of the formula (I) are those in which
R$^1$ represents alkyl with 1 to 5 carbon atoms, alkoxyalkyl or alkylthioalkyl with 1 to 5 carbon atoms per alkyl part, halogenoalkyl with 1 or 2 carbon atoms and up to 5 identical or different halogen atoms, such as fluorine or chlorine, cyanoalkyl with 1 to 5 carbon atoms in the alkyl part, trialkylsilylmethyl with 1 to 3 carbon atoms per alkyl part, alkenyl with 2 to 4 carbon atoms or alkinyl with 3 to 5 carbon atoms,
R$^2$ represents alkyl with 1 to 4 carbon atoms,
n represents 0 to 1, $R^3$ to $R^5$ are identical or different and represent hydrogen, alkyl or alkoxy with 1 to 4 carbon atoms, halogenoalkyl with 1 or 2 carbon atoms and up to 5 identical or different halogen atoms, such as fluorine or chlorine, halogenoalkoxy, halogenoalkylthio, halogenoalkylsulphinyl or halogenoalkylsulphonyl with 1 or 2 carbon atoms and up to 5 identical or different halogen atoms, such as fluorine or chlorine, per halogenoalkyl radical, N-halogenoalkyl-N-halogenoalkylthioamino with 1 or 2 carbon atoms and up to 5 identical or different halogen atoms, such as fluorine or chlorine, per halogenoalkyl radical, chlorine or fluorine and $R^6$ and $R^7$ represent hydrogen, fluorine, chlorine or trifluoromethyl, with the proviso that one of the radicals $R^3$ to $R^7$ is a fluorine-containing radical or at least 3 of the radicals $R^3$ to $R^7$ represent fluorine and/or chlorine.

Particularly preferred compounds of the formula (I) are those in which $R^1$ represents methyl, ethyl, n- or iso-propyl, 2,2-dimethyl-propyl, methoxymethyl, 2-methoxyethyl, ethoxymethyl, 2-ethoxyethyl, methylthiomethyl, 2-methylthio-ethyl, ethylthiomethyl, 2-ethylthio-ethyl, 2,2,2-trifluoroethyl, cyanomethyl, 2-cyanoethyl, trimethylsilylmethyl, allyl, methallyl, 3-propinyl or 1,1-dimethyl-3-propinyl, $R^2$ represents methyl, ethyl, n-propyl, iso-propyl, n-butyl, sec.-butyl, iso-butyl or tert.-butyl, n represents 0 or 1, $R^3$ to $R^5$ are identical or different and represent hydrogen, isopropyl, methoxy, tetrafluoroethoxy, trifluorochloroethoxy, trifluoromethyl, 2,2,2-trifluoroethyl, trifluoromethoxy, trifluoromethylthio, trifluoromethylsulphinyl, trifluoromethylsulphonyl, chlorodifluoromethoxy, chlorodifluoromethylthio, chlorodifluoromethylsulphinyl, chlorodifluoromethylsulphonyl, N-trifluoromethyl-N-dichlorofluoromethylthio-amino, chlorine or fluorine and $R^6$ and $R^7$ represent hydrogen or fluorine, with the proviso that one of the radicals $R^3$ to $R^7$ is a fluorine-containing radical or at least 3 of the radicals $R^3$ to $R^7$ represent fluorine and/or chlorine.

Compounds of the formula (I) which may be mentioned in particular are those in which $R^1$ represents methyl, ethyl, iso-propyl, 2,2-dimethylpropyl, trifluoroethyl or trimethylsilylmethyl, $R^2$ represents methyl, ethyl, iso-propyl or tert.-butyl and $R^3$ represents hydrogen, fluorine, trifluoromethyl or N-trifluoromethyl-N-dichlorofluoromethylthio-amino, $R^4$ represents hydrogen, trifluoromethyl, trifluoromethoxy, N-trifluoromethyl-N-dichlorofluoromethylthio-amino, methyl, trifluoromethylthio, fluorine or chlorine, $R^5$ represents hydrogen, iso-propyl, methoxy, trifluoromethyl, trifluoromethoxy, trifluoromethylthio, trifluoromethylsulphinyl, trifluoromethylsulphonyl, chlorodifluoromethoxy, chlorodifluoromethylthio, N-trifluoromethyl-N-dichlorofluoromethylthio-amino, fluorine or chlorine, $R^6$ and $R^7$ represent hydrogen or fluorine and n represents 0 or 1.

If, for example, 2,5-bis-(trimethylsilylmethyloxycarbonyl)-3-hydroxy-4-ethyl-thiophene and 3-trifluoromethyl-4-isopropylbenzoic acid are used as starting compounds for the preparation of the compounds of the formula (I) according to the invention and dicyclohexylcarbodiimide is used as the dehydrating agent, the course of the reaction can be represented by the following equation:

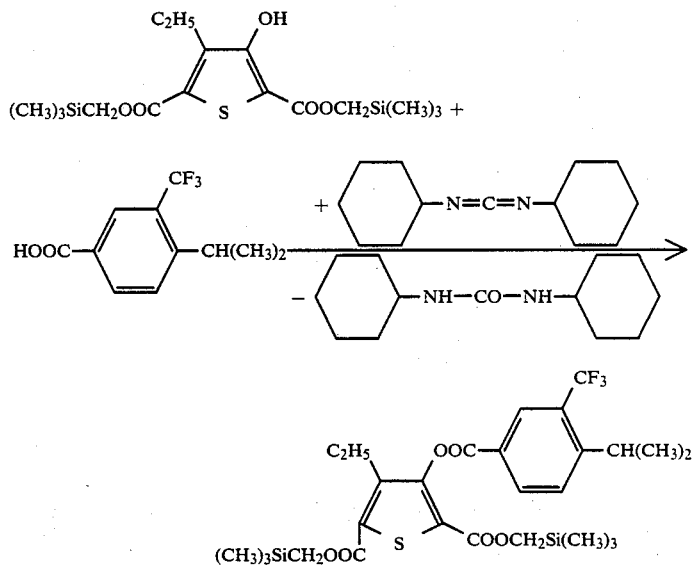

Formula (II) provides a general definition of the carboxylic acid derivatives required as starting substances for carrying out the process according to the invention. Most of the compounds are known, and they can be prepared by known processes.

Thus, some of the compounds can be prepared, for example, from fluorocarbonyl-N-(trifluoromethyl-sulphenyl)anilines and formic acid in the temperature range between 50° C. and 100° C. (compare DE-OS (German Published Specification) 1,810,580 and the corresponding British Patent Specification 1,229,083, DAS (German Published Specification) 1,293,754 and French Patent Specification 1,524,722).

Compounds which may be mentioned in particular here are: the halides and anhydrides of 2-, 3- and 4-trifluoromethylcinnamic acid, pentafluorobenzoic acid, 2-, 3- and 4-trifluoromethylbenzoic acid, 2-, 3- and 4-(N-trifluoromethyl-N-dichlorofluoromethylsulphenylamino)-benzoic and, 3-(N-trifluoromethyl-N-dichlorofluoromethylsulphenyl)-4-methyl-benzoic acid, 3-(N-trifluoromethyl-N-dichlorofluoromethylsulphenyl)-4-methoxybenzoic acid, 3-methyl-4-(N-trifluoromethyl-N-dichlorofluoromethylsulphenyl)-benzoic acid, 2,6-di-trifluoromethylbenzoic acid, 3,5-di-trifluoromethylbenzoic acid, 2-methoxy-6-trifluoromethylbenzoic acid, 2,3,4,5-tetrafluorobenzoic acid, 3,4,6-trifluorobenzoic acid, 3-chloro-4,5,6-trifluorobenzoic acid, 2,4,6-trifluoro-3,5-dichlorobenzoic acid, 3,5-dichloro-4-fluorobenzoic acid, 3- and 4-trifluoromethoxybenzoic acid, 3-trifluoromethyl-4-isopropylbenzoic acid, 3-chloro-4-trifluoromethoxybenzoic acid, 3-chloro-4-trifluoromethoxy-benzoic acid, 4-chlorodifluoromethoxy- and 4-chlorodifluoromethylthio-benzoic acid and 4-trifluoromethylsulphinyl- and 4-trifluoromethylsulphonyl-benzoic acid, and the corresponding free acids.

The 3-hydroxythiophene derivatives provided with a general definition by the formula (III) are furthermore required for the reactions to give the compounds according to the invention. Some of the starting compounds of the formula (III) are known, but they can be prepared by generally known processes, thus, for example, from thiodiacetic acid esters and 2-oxocarboxylic acid esters under alkaline conditions, for example under the action of potassium tert.-butylate, treatment with an acid being carried out after the condensation (compare European Patent 93,384 and DAS (German Published Specification) 1,020,641). The reaction can be illustrated by the following equation:

$R^2$—CO—CO—OR +

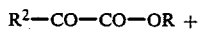

$R^1$—O—OC—CH$_2$—S—CH$_2$—CO—OR$^1$ —→

(III)

Compounds of the formula (IIIa)

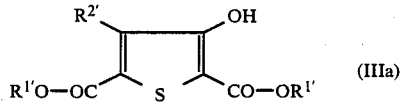

(IIIa)

in which
R$^{1'}$ represents 2,2-dimethylpropyl and R$^{2'}$ methyl or
R$^{1'}$ represents methyl and R$^{2'}$ iso-propyl
are new, but they can be prepared by the processes mentioned above.

Specific compounds which may be mentioned are: the methyl, ethyl, isopropyl, 2,2-dimethylpropyl, cyanomethyl, 2-cyanoethyl, 1-cyano-1-methyl-ethyl, 2,2,2-trifluoroethyl, 2-methoxyethyl, 2-butylthioethyl, 2-ethylthioethyl, trimethylsilylmethyl, allyl, methylallyl, propargyl and 1,1-dimethylpropargyl esters of 3-hydroxy-4-methyl-thiophene-2,5-dicarboxylic acid; and the 2,2,2-trifluoroethyl esters of 3-hydroxy-4-ethyl-, -4-propyl-, -4-isopropyl-, -4-butyl- and -4-tert.-butyl-thiophene-2,5-dicarboxylic acid.

Possible diluents for the process are all the organic solvents which are inert towards the reactants; polar solvents are preferably used. Examples which may be mentioned here are acetonitrile, acetone, chloroform, benzonitrile, dimethylacetamide, dimethylformamide, dimethylsulphoxide, chlorobenzene, ethyl acetate, dioxane, methyl ethyl ketone, methylene chloride and tetrahydrofuran.

The reactions can also be carried out in heterogeneous systems consisting of water and a water-immiscible solvent.

Organic bases, preferably tertiary amines, are used as acid-binders for the reaction. Bases which may be mentioned here are: quinoline, dimethylbenzylamine, dimethylaniline, ethyldicyclohexylamine, ethyldiisopropylamine, picoline, pyridine and triethylamine.

Carbodiimides, such as, for example, dicyclohexylcarbodiimide, are preferably used as water-binding agents when carboxylic acids are employed (formula II, X=OH).

The reaction temperatures and the reaction time are determined by the activity of the starting substances. In general, the reaction is carried out between about −50° and +80° C., preferably between −10° and +60° C.

For carrying out the process according to the invention, it is also possible to take, in an inert solvent, alkali metal or alkaline earth metal salts of the thiophene derivative to be reacted, or the salt is produced by adding alkali metal hydroxide solution, alcoholates or a corresponding alkaline earth metal compound to a mixture of the thiophene derivative and a high-boiling solvent and then carefully dehydrating the mixture or distilling off the alcohol, or by adding an alkali metal hydride or alkaline earth metal hydride.

If the condensation of the hydroxythiophene derivative with a fluorinated carboxylic acid is carried out with a carbodiimide, for example dicyclohexylcarbodiimide, for dehydration, the sparingly soluble urea formed can usually be separated off in a simple manner from the readily soluble compounds according to the invention.

Depending on the reaction conditions, the active compounds according to the invention are precipitated as crystals or they remain dissolved in the organic solvent and, after the solution has been washed out with water, can be precipitated by careful concentration of the solution or by addition of organic solvents of low polarity, such as cyclohexane, dibutyl ether or carbon tetrachloride. If necessary, water-miscible polar solvents must be removed by evaporation in vacuo after the reaction.

If the compounds according to the invention are dissolved in a water-miscible solvent, they can also be precipitated by addition of water.

Some of the compounds according to the invention decomposed at elevated temperature; in these cases, the melting points cannot be determined at all or can be determined only with a low accuracy. The existence of certain structural elements can be seen from the NMR spectra.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are used, for example, in plant protection for combating Pseudomonadaceae, Rhizobiaceae, Enterobacteriaceae, Corynebacteriaceae and Streptomycetaceae.

Some pathogens of fungal diseases which fall under the generaic terms listed may be mentioned as examples but not as a limitation: Botrytis species, such as, for example, *Botrytis cinerea;* Plasmopara species, such as, for example, *Plasmopara viticola;* Uromyces species, such as, for example, *Uromyces appendiculatus;* Spaerotheca species, such as, for example, *Spaerotheca fuliginea;* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *avenae;* Septoria species, such as, frr example, *Septoria nodorum;* Tilletia species, such as, for example, *Tilletia caries;* Xanthomonas species, such as, for example, *Xanthomonas oryzae;* Pseudomonas species, such as, for example, *Xanthomonas lachrymans;* Pyricularia species, such as, for example, *Pyricularia oryzae;* Pellicularia species, such as, for example, *Pellicularia sasakii;* Pyrenophora species, such as, for example, *Pyrenophora teres (conidia form: Drechslera, syn: Helminthosporium); Leptosphaeria species, such as, for example, Leptosphaeria nodorum;* Cochliobolus species, such as, for example, *Cochliobolus sativus;* (conidia form: Drechslera, syn: Helminthosporium) and Cercospora species, such as, for example, *Cercospora canescens.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as other fungicides, insecticides or acaricides, and as a mixture with fertilizers and growth regulators.

The active compounds can be used as such or in the form of their formulations or the use forms prepared therefrom by further dilution, such as ready-to-use solutions, emulsifiable concentrates, emulsions, foams, suspensions, wettable powders, pastes, soluble powders, dusting agents and granules. They are used in the customary manner, for example by watering, atomizing, spraying, scattering, dusting, foaming, brushing and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Example 1

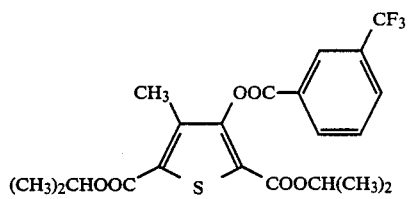

11.5 g of 2,5-bis-(isopropoxycarbonyl)-3-hydroxy-4-methyl-thiophene, 6 g of triethylamine and 100 ml of anhydrous acetonitrile are taken at 0° C. 8.3 g of 3-trifluoromethylbenzoyl fluoride are added dropwise in the course of 15 minutes. The reaction mixture is then kept at 58° C. for 2 hours. It is diluted with 400 ml of ethyl acetate, washed with water and with sodium bicarbonate solution and dried over sodium sulphate. After the solution has been evaporated and the residue has been heated at 60° C. under a high vacuum, 16.4 g of 2,5-bis-(isopropoxycarbonyl)-3-(3-trifluoromethylbenzoyloxy)-4-methylthiophene of refractive index $n_D^{20}=1.5101$ are obtained.

NMR 80 MHz CDCl$_3$ -  $CH(CH_3)_2$ 12 H, 2 d = 1.17 + 1.4 ppm
  $CH(CH_3)_2$ 2 H, m = 4.95–5.48 ppm
  $CH_3$-thiophene 3 H, s = 2.42 ppm
  benzoyl-H 2 H, m = 7.5–7.7 ppm
  2 H, m = 8.08–8.33 ppm The following compounds of the formula (I) can be prepared in the same manner:

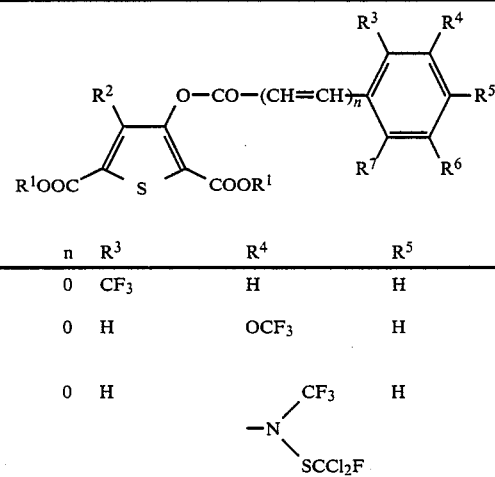

| Example No. | $R^1$ | $R^2$ | n | $R^3$ | $R^4$ | $R^5$ | $R^6$ | $R^7$ | Physical data (melting point: °C.) |
|---|---|---|---|---|---|---|---|---|---|
| 2 | $(CH_3)_2CH-$ | $CH_3$ | 0 | $CF_3$ | H | H | H | H | 78 from petroleum ether |
| 3 | $(CH_3)_2CH-$ | $CH_3$ | 0 | H | $OCF_3$ | H | H | H | 86 from petroleum ether |
| 4 | $(CH_3)_2CH-$ | $CH_3$ | 0 | H | $-N(CF_3)(SCCl_2F)$ | H | H | H | viscous mass |
| 5 | $(CH_3)_2CH-$ | $CH_3$ | 1 | $CF_3$ | H | H | H | H | 78 from petroleum ether |
| 6 | $CH_3$ | $CH_3$ | 0 | H | $CF_3$ | H | H | H | 136 from diisopropyl ether |
| 7 | $CH_3$ | $CH_3$ | 0 | H | $OCF_3$ | H | H | H | 105 |
| 8 | $(CH_3)_2CH-$ | $CH_3$ | 0 | $-N(CF_3)-SCCl_2F$ | H | H | H | H | viscous mass |
| 9 | $(CH_3)_2CH-$ | $CH_3$ | 0 | H | H | $-N(CF_3)-SCCl_2F$ | H | H | highly viscous mass |
| 10 | $CH_3$ | $CH_3$ | 0 | H | $-N(CF_3)(SCCl_2F)$ | H | H | H | 88 from petroleum ether |
| 11 | $CH_3$ | $CH_3$ | 0 | H | $-N(CF_3)-SCCl_2F$ | H | H | H | 78 from petroleum ether |
| 12 | $CH_3$ | $CH_3$ | 0 | $-N(CF_3)-SCCl_2F$ | H | H | H | H | 145 from petroleum ether |
| 13 | $(CH_3)_2CH-$ | $CH_3$ | 0 | H | $CF_3$ | $-CH(CH_3)_2$ | H | H | viscous mass |
| 14 | $(CH_3)_3C-CH_2-$ | $CH_3$ | 0 | H | $CF_3$ | H | H | H | viscous mass |
| 15 | $CH_3$ | $(CH_3)_2CH-$ | 0 | H | $CF_3$ | H | H | H | 123 from diisopropyl ether |
| 16 | $CH_3$ | $CH_3$ | 0 | $CF_3$ | H | H | H | H | 90 from petroleum ether |
| 17 | $(CH_3)_2CH-$ | $CH_3$ | 0 | H | H | $CF_3$ | H | H | 81 |
| 18 | $(CH_3)_2CH-$ | $CH_3$ | 0 | H | $SCF_3$ | H | H | H | viscous mass |

-continued

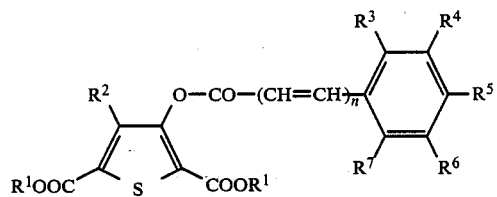

| Example No. | R¹ | R² | n | R³ | R⁴ | R⁵ | R⁶ | R⁷ | Physical data (melting point: °C.) |
|---|---|---|---|---|---|---|---|---|---|
| 19 | CH₃ | CH₃ | 0 | H | H | CF₃ | H | H | 108 |
| 20 | (CH₃)₃C—CH₂— | CH₃ | 0 | H | H | CF₃ | H | H | 70° |
| 21 | (CH₃)₂CH— | CH₃ | 0 | H | CF₃ | H | CF₃ | H | 83° |

The starting compounds of the formula (II) can be prepared, for example, as follows:

EXAMPLE a

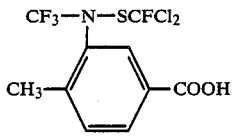

10 g of 3-N-(fluorodichloromethylmercapto)-N-trifluoromethylamino-4-methylbenzoic acid fluoride are dissolved in 50 ml of formic acid and the solution is heated at 90°–100° C. for 2 hours. Gas (CO, HF, HCOF) hereby evolves continuously. After cooling, the corresponding acid (9 g) crystallizes out and, after recrystallization from acetonitrile, has a melting point of 154°–156° C.

The following benzoic acids are obtained in an analogous manner from the associated acid fluorides:

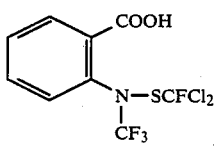 melting point 123° C.

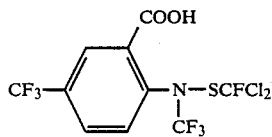 melting point 150° C.

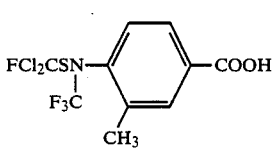 melting point 155° C.

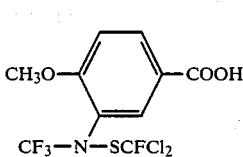 melting point 183° C.

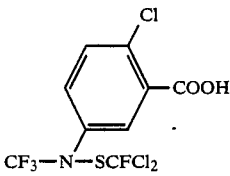 melting point 81–85° C.

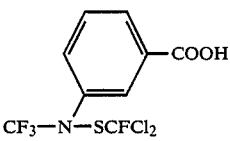 melting point 76–80° C.

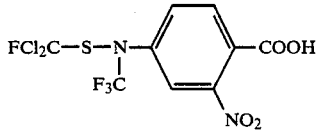 melting point 80–82° C.

EXAMPLE b

[structure: 3-COOH benzene with CF₃—N—SCF₂Cl]

32.5 g of 3-N-(difluorochloromethylmercapto)-N-trifluoromethylaminobenzoic acid fluoride are heated in 70 ml of formic acid for 2 hours. 17 g of the associated carboxylic acid of melting point 80°–82° C. crystallize out in the cold.

EXAMPLE c

The starting compounds of the formula (III) can be prepared by the instructions given in European Patent 93,384 and DAS (German Published Specification) 1,020,641. The following compounds are new:

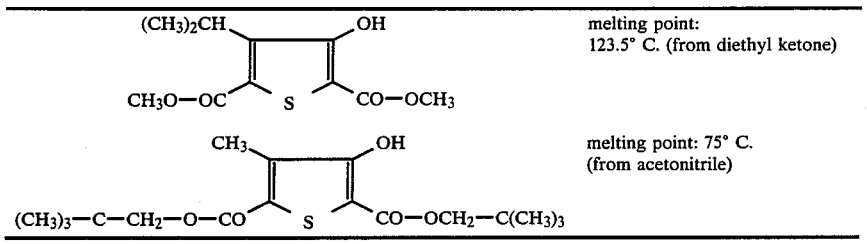

| | |
|---|---|
| | melting point: 123.5° C. (from diethyl ketone) |
| | melting point: 75° C. (from acetonitrile) |

EXAMPLE A

Sphaerotheca test (cucumber)/protective

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown by the compound 1 according to the invention.

EXAMPLE B

Podosphaera test (apple)/protective

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the powdery mildew of apple causative organism (*Podosphaera leucotricha*).

The plants are then placed in a greenhouse at 23° C. and a relative atmospheric humidity of about 70%.

Evaluation is carried out 9 days after the inoculation.

In this test, a clearly superior activity compared with the prior art is shown by the compounds according to the invention: 1, 3, 2 and 5.

EXAMPLE C

Pyrenophora teres test (barley)/protective

Solvent: 100 parts by weight of dimethylformamide
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of *Pyrenophora teres*. The plants then remain in an incubation cabinet at 20° C. and 100% relative atmospheric humidity for 48 hours.

The plants are placed in a greenhouse at a temperature of about 20° C. and a relative atmospheric humidity of about 80°.

Evaluation is carried out 7 days after the inoculation.

In this test, a clearly superior activity compared with the prior art is shown, for example, by the compounds according to the preparation examples: 1, 3, 2, 5 and 4.

It will be understood that the specification and examples are illustrative but not limitative of the present invention and that other embodiments within the spirit and scope of the invention will suggest themselves to those skilled in the art.

We claim:

1. An acyloxythiophene wherein such compound is selected from the group consisting of 2,5-bis-(isopropoxycarbonyl)-3-(3-trifluoromethylbenzoyloxy)-4-methyl-thiophene of the formula

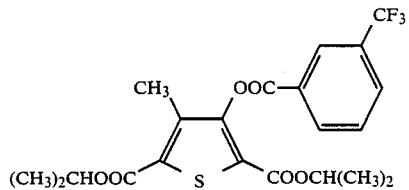

2,5-bis-(isopropoxycarbonyl)-3-(2-trifluoromethylbenzoyloxy)-4-methyl-thiophene of the formula

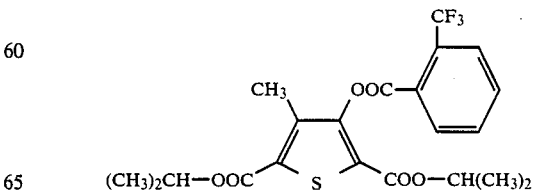

2,5-bis-(isopropoxycarbonyl)-3-(3-trifluoromethoxybenzoyloxy)-4-methyl-thiophene of the formula

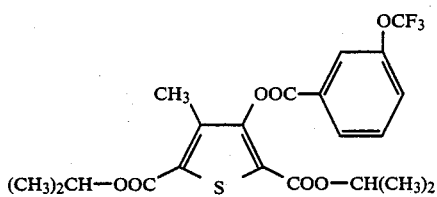

2,5-bis-(isopropoxycarbonyl)-3-(3-N-trifluoromethyl-N-dichlorofluoromethylthio-aminobenzoyloxy)-4-methyl-thiophene of the formula

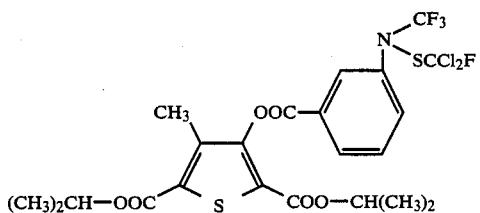

and 2,5-bis-(isopropoxycarbonyl)-3-(2-trifluoromethyl-cinnamoyloxy)-4-methyl-thiophene of the formula

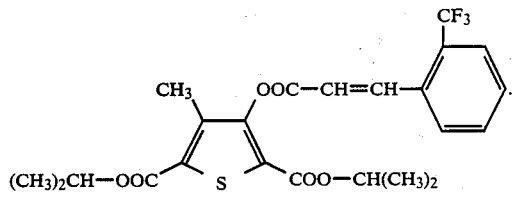

2. A method of combating fungi which comprises administering to such fungi or to a habitat thereof a fungicidally effective amount of a compound selected from the group consisting of:
2,5-bis-(isopropoxycarbonyl)-3-(3-trifluoromethylbenzoyloxy)-4-methyl-thiophene,
2,5-bis-(isopropoxycarbonyl)-3-(2-trifluoromethylbenzoyloxy)-4-methyl-thiophene,
2,5-bis-(isopropoxycarbonyl)-3-(3-trifluoromethoxybenzoyloxy)-4-methyl-thiophene,
2,5-bis-(isopropoxycarbonyl)-3-(3-N-trifluoromethyl-N-dichlorofluoromethylthio-aminobenzoyloxy)-4-methyl-thiophene and
2,5-bis-(isopropoxycarbonyl)-3-(2-trifluoromethyl-cinnamoyloxy)-4-methyl-thiophene.

* * * * *